United States Patent [19]

Ananthapadmanabhan et al.

[11] Patent Number: 4,690,892

[45] Date of Patent: Sep. 1, 1987

[54] PROCESS FOR THE RECYCLE OF PHASE-FORMING LIQUIDS OF MULTI-PHASE AQUEOUS SYSTEMS

[75] Inventors: Kavssery P. Ananthapadmanabhan, Spring Valley, N.Y.; Errol D. Goodard, Haworth, N.J.

[73] Assignee: Union Carbide Corporation, Danbury, Conn.

[21] Appl. No.: 828,656

[22] Filed: Feb. 12, 1986

Related U.S. Application Data

[63] Continuation-in-part of Ser. No. 728,242, Apr. 29, 1985, abandoned.

[51] Int. Cl.[4] .......................... C12N 9/00; C12N 9/28; C12N 9/20; C12N 9/42; C07K 3/12; C07K 3/28
[52] U.S. Cl. ..................................... 435/183; 435/202; 435/198; 435/209; 435/211; 435/814; 435/815; 435/816; 210/634; 530/412; 530/422; 530/424
[58] Field of Search .......................... 435/183, 212–234, 435/239, 816, 176, 180, 814, 815; 210/634

[56] References Cited

U.S. PATENT DOCUMENTS 4,343,735 8/1982 Menge et al. .................... 260/112 R
4,508,825 4/1985 Kim et al. ............................ 435/201

OTHER PUBLICATIONS

S. D. Flanagan, Affinity Phase Partitioning, *Receptor Biochem. Methodol.*, 2, 15–44 (1984).
G. Johansson and M. Andersson, Parameters Determining Affinity Partitioning of Yeast Enzymes Using Polymer-Bound Trizine Dye Ligands, *J. Chrom.*, 303, 39–51 (1984).
V. P. Shanbhag and G. Johansson, Interaction of Human Serum Albumin with Fatty Acids, *Eur. J. Biochem.*, 93, 363–367 (1979).
G. Birkenmeier, B. Tschechonien, and G. Koppers-chlager, Affinity Chromatography and Affinity Partition of Human Serum Pre-Albumin using Immobilized Remazol Yellow GGL *FEBS Letters,* 174, 162–166 (1984).
C. Axelsson and V. P. Shanbhag, Histone-Hydrocarbon Interaction, Partition of Histones in Aqueous Two-Phase Systems Containing poly(ethylene glycol)-Bound Hydrocarbons, *Eur. J. Biochem.*, 71, 419–423 (1976).
G. Johansson, The Effect of Poly(Ethyleneglycol) Esters on the Partition of Proteins and Fragmented Membranes in Aqueous Biphasic Systems, *Bioch. Biophys. Acta,* 451, 517–529 (1976).
G. Johansson and V. P. Shanbhag, Affinity Partitioning of Protein in Aqueous Two-Phase Systems Containing Polymer-Bound Fatty Acid *J. Chrom.*, 284 63–72 (1984).
G. Johansson, Comparison of Two Aqueous Biphasic Systems Used for the Separation of Biological Material, *J. Chrom.*, 150, 63–67 (1978).
G. Johansson, Studies on Aqueous Dextran-Poly(Ethylene Glycol) Two-Phase Systems Containing Charged Poly(ethylene Glycol) *Biochim. Biophys. Acta,* 222, 381–389 (1970).
S. D. Flanagan and S. H. Barondes, A Method for Purification of Proteins Using Specific Polymer-Ligands in Aqueous Polymer Two-Phase Systems, *J. Biol. Chem.*, 250, 1484–1489 (1975).

*Primary Examiner*—Lionel M. Shapiro
*Attorney, Agent, or Firm*—S. H. Flynn

[57] ABSTRACT

A method is disclosed for the recovery of biological material from an aqueous solution comprising contacting a water-insoluble, particulate binder with a solution containing biological material to produce a water insoluble biological material/binder composition which may then be recovered. The aqueous solutions may then be recycled.

19 Claims, No Drawings

PROCESS FOR THE RECYCLE OF PHASE-FORMING LIQUIDS OF MULTI-PHASE AQUEOUS SYSTEMS

This application is a continuation-in-part of U.S. Ser. No. 728,242, filed Apr. 29, 1985, now abandoned.

This invention relates to a process for the recovery and subsequent recycle of phase-forming liquids, such as polyethylene glycols, from aqueous systems, such as those employed in the separation of biological material. More particularly, it is directed to the removal of substances such as enzymes from at least one phase-forming liquid, thereby allowing reuse of the liquid. The removal of material is accomplished through its adsorption on a water-insoluble, inert solid binder introduced into the phase-forming liquid and subsequent removal of the enzyme/binder composition from solution, thereby allowing recycle of the phase-forming liquid.

BACKGROUND OF THE INVENTION

The potential applications for biologically active proteins have greatly increased. Commercial implementation of this technology now frequently depends on the ability to isolate these substances at reasonable cost. Until recently, separation technology which could support industrial applications was limited to filtration and centrifugation. However, these techniques are extremely dependant upon particle size and therefore approach their limit of usefulness during the harvest of even small intact microorganisms. The problems encountered are therefore greatly increased during the attempted isolation of intracellular components from ruptured cells where component size is, of course, greatly reduced.

The process of affinity partitioning using two phase aqueous systems has been suggested for some separations. Affinity partitioning basically involves the formation of multiple, distinct phases in a common solvent following the addition of materials, such as polymers, which produce immiscible phases when in solution, and the selective affinity of a molecule for one phase over the other.

Aqueous two phase systems have been known since the late nineteenth century from the work of Beijerinck who published has findings regarding aqueous phase formation with agar and gelatin. As affinity partitioning is not dependant upon particle size as are conventional techniques such as filtration and centrifugations it offers the potential of improved recovery of cellular components. The use of affinity partitioning in the isolation of enzymes from other cellular matter is disclosed in U.S. Pat. No. 4,144,130. Affinity partitioning technology has further been employed to date in the recovery of interferon (U.S. Pat. No. 4,343,735), the isolation of human coagulation factors VII and VIIa (U.S. Pat. No. 4,470,969) and the isolation of deoxyribonucleic acid (U.S. Pat. No. 4,207,200).

A number of systems suitable for the separation of enzymes are known, for instance those described in Albertson, P. A., *Partition of Cell Particles and Macromolecules*, Uppsala, 1st edition (1960), 2nd edition (1971) and U.S. Pat. No. 3,897,414. The aqueous systems most commonly employed are those consisting of polyethylene glycol/dextran or polyethylene/glycol/water-soluble inorganic salt.

Due to the relatively low concentration of enzyme in the feed liquors, the relatively low efficiencies at which these processes may operate and the large quantities of product desired, commercial application of two phase aqueous system technology requires the use of large volumes of the phase-forming liquids. Recycle of these liquids would therefore greatly increase the commercial viability of this technology. However, the isolation of product from a system and subsequent recycle of liquids must be accomplished without adversely effecting the properties of the material which is partitioned in the system. For instance, the activity of enzymes isolated through use of multi-phase systems should not be adversely affected to an undue degree. Moreover, isolation of material from the system's phase-forming liquids should be accomplished in a manner such that neither the liquids nor the isolated material require extensive processing to place it in a form which can be employed in its final application.

The applicants have therefor sought to provide through the present invention a method for recycle of the phase-forming liquids of an aqueous system having at least two aqueous phases and containing biological material, such as enzymes, through the introduction of a water-insoluble inert binder material onto which biological material, such as enzymes, may be adsorbed. The binder with its adsorbed material may then be readily recovered through conventional techniques, such as filtration or centrifugation, leaving the liquid available for recycle. The biological material may be released from the binder or, if its final application allows, it may be used in this combined form.

SUMMARY OF THE INVENTION

This invention relates to a process for the recovery and subsequent recycle of phase-forming liquids from aqueous systems having at least two phases, such as those employed in the separation of biological material. More particularly, it is directed to the removal of biological material, such as enzymes, from at least one phase-forming, liquid, thereby allowing reuse of the liquid. The removal of material is accomplished through its adsorption on a water-insoluble, inert solid binder introduced into the phase-forming liquid.

DETAILED DESCRIPTION OF THE INVENTION

The methods of the instant invention may generally be applied in aqueous systems having at least two phases such as those employed in the isolation and recovery of biological materials, such as enzymes.

While the further description of the invention shall be discussed in terms of the recycle of phase-forming liquids from two phase systems used in the isolation of enzymes, it is understood that also within the scope of the instant invention is the recycle of phase-forming liquids from systems containing biological material other than enzymes as well as with systems containing more than two phases.

The procedures claimed herein are also applicable to the recycle of phase-forming liquids used in the isolation of enzymes from aqueous solutions containing intact cells or fragments thereof, where the process of affinity partitioning, as discussed below, is employed to isolate the enzyme directly from the enzyme-containing phase of the multi-phase system, thereby consolidating the usual steps of cell fragmentation and enzyme isolation.

Enzymes, like other proteinaceous materials, may be electrochemically neutral or may exhibit an anionic or cationic character, meaning having a net negative or positive charge, respectively, depending on the pH of their environment. The pH at which the enzyme is neutral is its isoelectric point, which can be determined through gel electrophoresis characterized by the absence of enzyme migration. Typically, at a pH above the isoelectic point of a given enzyme, it will exhibit an anionic character. Below its isoelectric point, a cationic character will be exhibited. In the case of the preferred enzyme, alkaline protease, its isoelectric point is in the range of about 7 to about 9.

Examples of two phase aqueous systems which have been used in the isolation of biological matter and containing at least two polymers are: dextran/water-soluble copolymer or sucrose and epichlorohydrin, dextran/hydroxypropyl-dextran, polyethylene glycol/dextran sulphate, charged polyethylene glycol/dextran, dextran/polyethylene glycol, polypropylene glycol/methoxypolyethylene glycol, polypropyleneglycol/polyethylene glycol, polypropylene glycol/polyvinyl alcohol, polypropylene glycol/polyvinyl pyrrolidone, polypropylene glycol/hydroxypropyldextran, polypropylene glycol/dextran, polyethylene glycol/polyvinyl alcohol, polyethylene glycol/polyvinyl pyrrolidone, polyethylene glycol/water-soluble copolymer of sucrose and epichlorohydrin, polyethylene glycol/water-soluble starch, polyethylene glycol/glycogen, polyvinyl alcohol/methyl cellulose, polyvinyl alcohol/hydroxypropyl-dextran, polyvinyl alcohol/dextran, polyvinyl pyrrolidone/methyl cellulose, polyvinyl pyrrolidone/dextran, methyl cellulose/hydroxypropyl dextran, methyl cellulose/dextran and ethylhydroxyethyl cellulose/dextran. Also known are systems involving methoxy- or ethoxy-polyethylene glycol in the place of or in conjunction with polyethylene glycol. For purposes of this application, polyethylene glycol shall include these derivatives, such as the methoxy or ethoxy-substituted materials.

Other aqueous systems which have been used in the isolation of these materials are those composed of at least one polymer and at least one salt or organic solvent. The polymer may be chosen from those listed immediately above and is preferably polyethylene glycol, polypropylene glycol, polyvinyl pyrrolidone, a polysaccharide or a water-soluble derivative thereof. Representative examples of salts are magnesium sulfate, potassium sulfate and sodium chloride. The organic solvents may include propylalcohol, glycerol and 2-butoxyethanol.

The systems may further contain additional materials including pH buffers such as tris(hydroxymethyl)-aminomethane, morpholine ethane sulfonate and citrate, which may be employed with saline. These aqueous systems may also contain additional salts and organic solvents, adjuvants, etc.

The most widely used two-phase systems are composed of aqueous solutions of polyethylene glycol and either dextran or water-soluble, inorganic salt solutions. Typical systems employ, for example aqueous solutions of 1–50 wt. % of polyethylene glycols preferably, having average molecular weights of from 5,000 to 20,000 in conjunction with 2–25 wt. % aqueous solutions of dextran or 3–20 wt. % aqueous solutions of inorganic salts such as sodium sulfate.

The type of biological material contained in the system is not critical. Systems employed in the isolation of enzymes such as amylases, cellulases, dextranase, invertases, isomerases, lipases, oxidases, pectinases and proteases may therefore be employed in the process of the instant invention. Preferred is the treatment of systems containing proteolytic enzymes, in particular alkaline protease.

The binder may be any material which (1) is insoluble in the aqueous medium, (2) is inert with respect to the aqueous medium, (3) does not unduly degrade the potency of the biological material which adsorbs on it and (4) effectively interacts with the material to form an insoluble composition in the aqueous medium. The binders may be both porous and non-porous. Binders possessing a high surface area are preferred. Particulate materials are therefore preferred. Also preferred are binders which are acidic in nature. Representative of binders which may be employed are carbond such as activated carbon, graphite and carbon fiber, inorganic oxides such as metal oxides, magnesias, silicas, titanias, alpha-aluminas, aluminosilicates, aluminophosphates and silica-aluminophosphates. Other examples are sintered glasses, silicon carbide aggregates, pumice, firebrick, diatomaceous earths, pulverized/sintered plastics and organic resins with carboxylic functionality. Preferred in the treatment of alkaline protease-containing systems is titanium dioxide.

As with enzymes, each type of binder has been found to possess an isoelectric point. However, in most cases, the isoelectric points of a binder and an enzyme are not identical. Therefore, through proper manipulation of the reaction conditions to which both the enzyme and the binder are exposed, it is possible to impose opposite net charges on the enzyme and the binder. While the applicants do not wish to be limited in the explanation of the exact nature of the interaction involved in the formation of the enzyme-binder composition, it appears that the establishment of oppositely charged species at a given pH gives rise to the composition due to an electrostatic interaction.

It is further possible to employ non-ionic binders in the instant process. The enzyme adsorbed on the non-ionic binder may be in an anionic, cationic or non-ionic state. Due to lack of electrostatic interaction as is present in the case of ionic binder as discussed above, it appears that formation of the enzyme/binder composition is due to polar bonding.

It is further possible to employ adjuvants to pretreat the binder prior to its introduction into the system. These substances are inert to the aqueous medium and do not degrade the potency of the enzyme with which they will contact. Representative of the binder adjuvants are cationic, anionic or non-ionic polymers.

Examples of anionic polymers are polycarboxylic acids such as polyacrylic acid and polymethacrylic acid. Further examples of anionic substances useful in the present invention are polyphosphoric acids, carboxymethylcellulose and the co-polymer of maleic anhydride and vinyl methyl ether. Examples of cationic binders are quaternized vinyl pyrrolidone/aminoethyl methacrylane copolymer, adipic acid/dimethylaminohydroxy propyl diethylene triamine copolymer, poly (N,N-dimethyl-3,5 methylene piperidinium chloride, acrylamide/beta methacryloxy ethyl trimethyl ammonium chloride, quaternized guar gum derivative, chitosan, "Polymer JR." (a cationic cellulosic polymer marketed by Union Carbide Corporation) and polyethylene imine. Examples of non-ionic binders which may be employed are water-soluble, low molecule weight phenolic resins such as the formaldehyde-containing resin manufactured by Union Carbide Corporation and marketed as "Bakelite BRL 511" and the formaldehyde-containing resin manufactured by Borden Company and marketed as "Cascothen 511".

Since the binder simply provides a substrate for the adsorption of the enzyme rather than chemically reacting with it, the binder need not be present in any specific amounts. Rather, its concentration is dictated by both maximization of enzymatic recovery and economic considerations. Surface area to the binder and particle size are factors which must be taken into account in the optimization of a recovery operation. The liquid phase/binder mixture must however retain sufficient fluidity to be manageable in continuous, commercial systems. Moreover, while a sufficient quantity of binder must be present to ensure adequate recovery of the enzyme contained in the solution, the presence of great excesses of binder is simply economically wasteful.

Recovery of the enzyme/binder composition from solution may be accomplished through the use of conventional techniques, such as simple filtration or centrifugation. The liquid from which the enzyme has been recovered can then be recycled back into the existing two phase system or used in the establishment of a new system.

If the enzyme/binder composition formed in the practice of the present invention is to be itself employed in this form rather than disassociated, the binder materials should of course be compatible with the intended final application of the composition. As the binder material is relatively inert, this should not present a great limitation. In the case of an alkaline protease/binder composition, the complex is readily compatible with cleansing formulations. In fact, binders such as zeolites are now commonly present in commercial detergent formulations as sequestering agents. Use of this composition is therefore extremely attractive for incorporation into detergent formulations as both its component parts may enhance the activity of the final formulation.

Recycle of phase-forming liquids from enzyme-containing multi-phase systems through use of the instant invention may be accomplished through simple introduction of the binder into the enzyme-containing liquid for a period adequate and accompanied with sufficient agitation to ensure adequate exposure of the binder and enzyme. The enzyme-containing solution may be obtained through isolation of one phase of an aqueous two phase system. The remaining phase may be discarded or, more preferably also be treated through use of the claimed invention and recycled for later use in the reestablishment of a multi-phase system. Alternatively, the binder may be introduced into the multi-phase system rather than into one of its isolated phases. The conditions present during use of the claimed process are not critical except as noted. Temperatures and pressures should be such that they do not denature the enzyme or diminish its potency beyond limits acceptable to it final application.

The pH of the solution should be maintained at a level at which formation of the composition is promoted. This will, of course, vary with the individual enzymes and binders employed as explained above. In the case of the alkaline protease/binder composition, the pH of the solution should be less than about 7, preferably 6 or less, most preferably about 5 to about 6.

The protease/binder composition may be recovered from the mixing apparatus by conventional means, such as centrifugation or filtration.

The following examples illustrate embodiments of the present invention and are not to be construed as a limitation of its scope.

These examples are offered to demonstrate formation and isolation of the enzyme/binder composition from the isolated aqueous phase of a multi-phase system and the retention of enzymatic activity by the isolated enzyme.

All parts and percentages are by weight unless otherwise indicated. All temperature values are given in degrees Celsius.

CONTROL

Approximately 0.5 grams of a liquid alkaline protease-containing composition manufactured by Miles Laboratories and marketed under the designation APL 440 were mixed with 499.5 g. of 0.05M potassium phosphate solution (hereinafter referred to as Solution A). According to its manufacturer, APL 440 possesses an activity of approximately 440,000 DAPU/kg. A DAPU, or Detergent Alkaline Protease Unit, is defined as that activity which will liberate four nanomoles of tyrosine per minute under specified conditions. The method employed in the determination of this activity will be set forth below. The alkaline protease content of APL 440 is not known. Therefore, for the purposes of the following experiments, APL 440 is assumed to be 100% pure and its activity is assumed to be 440,000 DAPU/kg. Solution A is therefore presumed to contain about 0.1% alkaline protease and an activity of about 440 DAPU/kg.

Determination of Activity

In the experiments presented below, the determination of enzymatic activity is based on a proteolytic hydrolysis of a Hammerstein casein substrate in synthetic tap water over a period of 40 minutes at 40 degrees Celsius. The synthetic tap water possesses a hardness of 269 ppm of calcium carbonate and, a pH of 8.5. Unhydrolysed substrate is precipitated with trichloroacetic acid and removed by centrifugation. The solubilized casein is then determined spectrophotometrically.

The following stock solutions were prepared.

Sol. 1. 500 ml. distilled water containing 12.6 g. of calcium chloride dihydrate.

Sol. 2. 500 ml. distilled water containing 7.0 g. of magnesium chloride.

Sol. 3. 500 ml distilled water containing 10.5 g of anhydrous sodium bicarbonate.

STW—Synthetic tap water prepared by introducing 10 ml. of each of solutions 1, 2 and 3 into 970 ml. of distilled water.

STPP—Sodium tripolyphosphate solution (2.0%) was prepared by introducing 20.9 g. of sodium tripolyphosphate and 10 ml. of each of solutions 1, 2 and 3 into 970 ml. of distilled water with continuous agitation until completely dissolved. The pH of the solution was then adjusted to 8.5 +/ 0.1 using 0.1N HCL. Any precipitate was allowed to settle but was not removed from the solution.

Sol. 4. 400 ml. distilled water containing 90.3 g of anhydrous sodium acetate diluted to 500 ml. with distilled water.

Sol. 5. 350 ml. distilled water containing 150 g of glacial acetic acid.

Sol. 6. 47.5 ml. of distilled water containing 2.5 ml. of polysorbate 80.

TCA—The trichloroacetic acid (TCA) reagent was prepared by mixing 18 g. of TCA with 100 ml. of each of Solutions 4 and 5 and 4 ml. of Solution 6. The resulting solution was then diluted to one liter with distilled water.

THAM—400 ml. of STW containing 18.17 g. of tris-hydroxy-methyl amino methane.

A casein-containing solution was then prepared by adding, under constant agitation, 6.67 g. (moisture free basis) of Hammerstein casein to 350 ml. of the STW solution. Stirring was continued for ten mintues. 50 ml. of THAM solution was then added and stirred continuously for 10 minutes. The resulting solution was then allowed to equilibrate in a water bath having a temperature of $40 +/- 0.1$ degrees C. for 30 minutes. The pH of the solution was then adjusted to $8.5 +/- 0.1$ at 40 degrees C. with 1N NaOH. The solution was allowed to cool to room temperature and was then diluted to 500 ml. with STW solution. It should be noted that this solution degrades overtime and therefore must be prepared daily.

An enzyme-containing solution was then prepared in the STPP solution such that one ml. of the final dilution had an activity of 20–40 DAPU/ml. The pH of the final dilution was adjusted to 8.5 using either 1N HCL or 1N NaOH.

A 5 ml. sample of the enzyme-containing solution was then transferred to a $25 \times 150$ mm. test tube and placed in a constant temperature water bath maintained at 40 degrees C. 5 ml. portions of the casein substrate are then pipetted into each of three $25 \times 150$ mm test tubes, one of which was to be used as a standard for comparative purposes. These samples were then placed in the water bath and allowed to equilibrate at 40 degrees C. for 10 minutes.

Noting the exact time, 1 ml. of the enzyme solution were then introduced into two of the substrate-containing test tubes which were then stoppered. After exactly 40 minutes, 5 ml. of TCA solution were added to each tube and mixed by gentle swirling of their contents.

An enzyme blank was then prepared by adding 5 ml. of TCA solution into the remaining substrate-containing test tube and mixing its contents by gentle swirling.

All test tubes were then placed in the water bath and incubated for 30 minutes. After exactly 30 minutes had passed, the test tubes were transferred to an ice bath where they were allowed to remain for about 5 minutes. The tubes were then centrifuged at about 3000 ppm for about 15 minutes. The supernatant was then recovered into clean cuvettes. The absorbance of UV radiation (275 nm) by each sample is recorded.

The absorbance data was then used to calculate the activity of the enzyme through the formula set forth immediately below.

$$DAPU/g = A \times 11 / 0.00552 \times 40 \times W$$

wherein A is absorbance difference between the enzyme/substrate sample and the enzyme blank, 11 is the final reaction volume, 0.00552 is the absorbance of 4 nanomoles of tyrosine, 40 is the elapsed time in minutes and W is the weight in grams added to the reaction mixture in one 1 ml. aliquoe.

Through use of the method described immediately above, it was determined that the alkaline protease solution used in the experiments presented below possessed an activity of about 396,800 DAPU/dg., or about 90.2% of its claimed activity.

EXAMPLE 1

A 20 wt. % polyethylene glycol solution, hereinafter referred to Solution B, was prepared by dissolving 20. g. of a polyethylene glycol having an average molecular weight of 1450 and marketed by Union Carbide Corporation under the designation CARBOWAX Polyethylene glycol (PEG) 1450, in 100. ml. of distilled water. Five grams of Solution B were then added to 45 g. of a 0.05 M solution of potassium phosphate. This was followed by the addition of 0.1 g. of alumina, marketed by Union Carbide Corporation under the product designation "Linde A" and 0.9 g. of the alkaline protease-containing Solution A. The resulting suspension was then diluted to a final mass of 10 grams with additional 0.05M potassium phosphate solution. The resulting suspension was then agitated for 30 minutes. Its pH was determined to be about 7. The mixture was then centrifuged at a speed of about 3000 ppm for about 15 minutes to produce a pellet. The supernatant which could be recycled to establish a two phase system, was removed and retained for later analysis.

The pellet was then resuspended in sufficient STPP Solution to produce a solution having a final mass of 10.00 grams. The resulting solution was then analyzed for proteolytic activity as described above.

The activity of the suspension was found to be about 15.6% of the original activity.

The supernatant was also analyzed and was found to possess about 64.4% of original activity.

EXAMPLE 2

The procedure of Example 1 was repeated except that the alumina employed in Example 1 was replaced with an equal mass of powdered titanium dioxide, manufactured by Aldrich Chemical. The pH of the solution was measured and found to be about 7. The resuspended pellet and decanted supernatant were then analyzed for proteolytic activity as described above.

The suspension was found to possess about 32.2% of original activity while the supernatant was found to possess about 34.4% of original activity.

EXAMPLE 3

The procedure of Example 2 was duplicated except that 0.2 grams of titanium dioxide were employed. The pH of the solution was measured and found to be about 7. The resuspended pellet and decanted supernatant were then analyzed for proteolytic activity as described above.

The suspension was found to possess about 47.8% of original activity while the supernatant was found to possess about 35.6% of original activity.

EXAMPLE 4

The procedure of Example 2 was repeated except that 0.3 grams of titanium dioxide were employed. The pH of the solution was measured and found to be about 7. The resuspended pellet and decanted supernatant were then analyzed for proteolytic activity as described above.

The suspension was found to possess about 77.8% of original activity while the supernatant was found to possess about 38.9% of original activity.

EXAMPLE 5

The procedure of Example 2 was repeated except that the solid employed was a zeolite in the amount of 0.1 grams. The pH of the solution was measured and found to be about 7. The resuspended pellet and decanted supernatant were then analyzed for proteolytic activity as described above.

The suspension was found to possess about 3.3% of original activity while the supernatant was found to possess about 94.4% of original activity.

EXAMPLE 6

The procedure of Example 5 was duplicated except that the solid employed was a calcined alumina silicate (marketed by Englehard of Edison N.J. under the product designation Santitone #5). The solid was employed in an amount of 0.1 grams. The pH of the solution was measured and found to be about 7. The resuspended pellet and decanted supernatant were then analyzed for proteolytic activity as described above.

The suspension was found to possess about 25.6% of original activity while the supernatant was found to possess above 77.8% of original activity.

EXAMPLE 7

The procedure of Example 3, using 0.2 grams of titanium oxide, was duplicated except that the pH of the resulting suspension was lowered to about 6 through the addition of dilute HCl prior to agitation. The resuspended pellet and decanted supernatant were then analyzed for proteolytic activity as described above.

The suspension was found to possess about 83.3% of original activity while the supernatant was found to possess about 11.1% of original activity.

EXAMPLE 8

The procedure of Example 2 was duplicated except that the solid was first pretreated through contact with 1.0 g. of a 1.0% aqueous solution of polyacrylic acid, having an average molecular weight of about 150,000. The excess polyacrylic acid was then removed. The pretreated solid was then added to the enzyme-containing solution. The resuspended pellet and decanted supernatant were then analyzed for proteolytic activity as described above.

The suspension was found to possess about 14.4% of original activity while the supernatant was found to possess about 58.9% of original activity.

EXAMPLE 9

The procedure of Example 8 was duplicated except that a 10% aqueous solution of a polyethylene glycol having an average molecular weight of 1450 and marketed by Union Carbide Corporation under the tradename CARBOWAX Polyethylene glycol 1450 was added to the enzyme-containing solution. The resuspended pellet and decanted supernatant were then analyzed for proteolytic activity as described above.

The suspension was found to possess about 16.7% of original activity while the supernatant was found to possess about 65.6% of original activity.

From the data set forth above, it can be seen that an enzyme can be recovered from solution with substantial retention of its activity. Moreover, after removal of the enzyme/binder, the liquid is free to be recycled thereby allowing its use in the establishment of an aqueous multi-phase system as well as the retention and later recovery of the enzymatic activity which it may still contain.

We claim:

1. A method for recycling the phase-forming liquids of an aqueous system having at least two aqueous phases and which contains biological material in at least one phase thereof, comprising:
   a. introducing into at least one of said liquid phases containing biological material a water-insoluble, particulate, inert inorganic binder under conditions suitable for the formation of a biological material/binder composition;
   b. recovering the biological material/binder composition from said liquid phase, and
   c. recycling at least a portion of the liquid phase from which biological material has been recovered to the two phase system.

2. The method of claim 1 wherein the biological material is an enzyme selected from the group consisting of amylase, cellulase, dextranase, invertase, isomerase, lipase, oxidase, pectinase and protease.

3. The method of claim 1 wherein the biological material comprises alkaline protease.

4. The method of claim 1 wherein the binder comprises an inorganic oxide.

5. The method of claim 1 wherein the binder is selected from the group consisting of diatomaceous earths, magnesias, silicas, alpha-aluminas, titanias, aluminosilicates, aluminophosphates, silica-aluminophosphates, sintered glasses, pumice and firebrick.

6. The method of claim 5 wherein the binder comprises titanium dioxide.

7. The method of claim 1 wherein the biological material comprises alkaline protease and the binder comprises titanium dioxide.

8. The method of claim 1 wherein the binder is selected from the group consisting of silicon carbide aggregates, pulverized/sintered plastics, activated carbon, carbon fiber, graphite and organic resins having carboxylic functionally.

9. The method of claim 1 further comprising contacting the binder with an adjuvant prior to its introduction into the phase-containing biological material, said adjuvant being selected from the group consisting anionic, cationic and non-ionic polymers.

10. The method of claim 9 wherein the adjuvant is a cationic polymer selected from the group consisting of quaternized vinyl pyrrolidone/aminoethyl methacrylate copolymer, adipic acid/dimethylaminohydroxy propyl diethylene triamine copolymer, poly (N,N-dimethyl-3,5 methylene piperidinium chloride), acrylamide/beta methacryloxy ethyl trimethyl ammonium chloride, quaternized guar gum derivative polyethylene amine, cationic cellulosic polymers and mixtures thereof.

11. The method of claim 9 wherein the adjuvant comprises a polycarboxylic acid.

12. The method of claim 11 wherein the polycarboxylic acid is selected from the group consisting of polyacrylic acid and polymethacrylic acid.

13. The method of claim 9 wherein the adjuvant is an anionic polymer selected from the group consisting of polyphosphoric acid, carboxymethylcellulose and the copolymer of maleic anhydride and vinyl methyl ether.

14. The method of claim 1 further comprising adjusting the pH of the phase containing biological material prior to the recovery of the biological material/binder composition such that formation of the biological material/binder composition is promoted.

15. The method of claim 1 further comprising isolating a liquid phase from said aqueous system having at least two phases prior to contacting said isolated phase with said binder.

16. A method for recycling polyethylene glycol from a two-phase aqueous system containing biological material wherein one phase of said aqueous system comprises polyethylene glycol and biological material comprising
   a. isolating the polyethylene glycol-containing phase from said two phase system;
   b. introducing into the isolated phase a water-insoluble particulate, inert solid binder under conditions suitable for the formation of a biological material/binder composition;
   c. recovering the biological material/binder composition from the isolated polyethylene glycol-containing phase, and
   d. recycling at least a portion of the polyethylene glycol-containing phase to the two phase system.

17. The method of claim 16 wherein the binder is titanium dioxide and the biological material is alkaline protease.

18. The method of claim 16 wherein the isolated phase is provided with a pH of less than about 7 prior to step (c).

19. The method of claim 18 wherein the pH is from about 5 to about 6.

* * * * *